(12) United States Patent
Ray et al.

(10) Patent No.: US 8,831,884 B2
(45) Date of Patent: Sep. 9, 2014

(54) METHODS OF DETERMINING WATER DROPLET SIZE DISTRIBUTIONS OF CLOUDS

(75) Inventors: Mark D Ray, Burnsville, MN (US); Kaare J Anderson, Farmington, MN (US); Michael P Nesnidal, Shakopee, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 392 days.

(21) Appl. No.: 13/280,877

(22) Filed: Oct. 25, 2011

(65) Prior Publication Data

US 2013/0103316 A1 Apr. 25, 2013

(51) Int. Cl.
| | |
|---|---|
| G06F 19/00 | (2011.01) |
| G01N 21/00 | (2006.01) |
| G01N 15/02 | (2006.01) |
| G01S 17/95 | (2006.01) |
| G01N 15/00 | (2006.01) |
| B64D 15/20 | (2006.01) |

(52) U.S. Cl.
CPC ............ G01S 17/95 (2013.01); G01N 15/0211 (2013.01); *G01N 2015/0026* (2013.01); *B64D 15/20* (2013.01)
USPC .............................................. 702/3; 356/342

(58) Field of Classification Search
None
See application file for complete search history.

(56) References Cited

U.S. PATENT DOCUMENTS

| | | | | |
|---|---|---|---|---|
| 4,537,507 | A | * | 8/1985 | Hess .............................. 356/336 |
| 5,619,324 | A | * | 4/1997 | Harvill et al. ................. 356/336 |
| 1,001,918 | A1 | | 1/2011 | Ray et al. |
| 2004/0036630 | A1 | * | 2/2004 | Jamieson et al. .............. 340/962 |
| 2008/0208511 | A1 | * | 8/2008 | Trainer ......................... 702/128 |
| 2008/0221814 | A1 | * | 9/2008 | Trainer ............................ 702/70 |
| 2010/0026981 | A1 | * | 2/2010 | Spinelli et al. ................ 356/4.01 |
| 2010/0225913 | A1 | * | 9/2010 | Trainer ......................... 356/338 |
| 2010/0231909 | A1 | * | 9/2010 | Trainer ......................... 356/336 |

OTHER PUBLICATIONS

Gilles Roy, Luc Bissonnette, Christian Bastille, and Gilles Vallee, Retrieval of droplet-size density distribution from multiple-field-of-view cross-polarized lidar signals: theory and experimental validation, Aug. 1999, Applied Optics, vol. 38, No. 24, p. 5202-5211.*

Carlton W. Ulbrich, Natural Variations in the Analytical Form of the Raindrop Size Distribution, Oct. 1983, Journal of Climate and Applied Meteorology, vol. 22, p. 1764-1775.*

Natasha L. Miles, Johannes Verlinde, and Eugene E. Clothiaux, Cloud Droplet Size Distributions in Low-Level Stratiform Clouds, Jan. 2000, Journal of the Atmospheric Sciences, vol. 57, p. 295-311.*

(Continued)

*Primary Examiner* — Toan Le
(74) *Attorney, Agent, or Firm* — Edwards Wildman Palmer LLP; Scott D. Wofsy; Joshua L. Jones

(57) ABSTRACT

In one aspect, methods of determining a size distribution of water droplets in a cloud are described herein. In some embodiments, a method of determining a size distribution of water droplets in a cloud comprises sampling a depth of the cloud with a beam of electromagnetic radiation, measuring a scattering signal of the electromagnetic radiation returned from the cloud over a range of field of view angles to provide a measured scattering curve $[p_{total}(\theta)]$, removing a portion of the measured scattering curve, replacing the removed portion with an extrapolation of the remaining measured scattering curve to provide an estimated scattering curve, and determining a first estimate droplet size distribution $[n^{(1)}(D)]$ from the estimated scattering curve.

31 Claims, 4 Drawing Sheets

(56) References Cited

OTHER PUBLICATIONS

A. R. Jameson, Microphysical Interpretation of Multi-Parameter Radar Measurements in Rain.Part II: Estimation of Raindrop Distribution Parameters by Combined Dual-Wavelength and Polarization Measurements, Jul. 1983, Journal of the Atmospheric Sciences,vol. 40, p. 1803-1813.*

Carlton W. Ulbrich, A Method for Measuring Precipitation Parameters Using Radar Reflectivity and Optical Extinction, Annales des Télécommunications, Annales des Télécommunications, Nov./Dec. 1977, vol. 32, Issue 11-12, p. 415-421.*

Jan Skov Pedersen, Analysis of small-angle scattering data from colloids and polymer solutions: modeling and least-squares fitting, Advances in Colloid and Interface Science ,1997, p. 171-210.*

Hogan, R. J., "Fast approximate calculation of multiply scattered lidar returns," Applied Optics, 2006, 45 (23), pp. 5984-5992.

Kohkanivsky, "Optical Properties of Terrestrial Clouds", Earth-Science Reviews 64, pp. 189-241 (2004).

Eloranta, E. W., "Practical model for the calculation of multiply scattered lidar returns," Applied Optics, 1998, 37 (12), pp. 2464-2472.

Shah, A. D., "Droplet Size Distribution and Ice shapes," American Institute of Aeronautics and Astronautics (AIAA) International Conference of Aircraft Inflight Icing, May 1996, pp. 1-20.

Roy, Bissonnette, Bastille, Vallee, "Estimation of cloud droplet size density distribution from multiple-field-of-view lidar returns," Opt. Eng.. 36(12) 3404-3415 (1997).

* cited by examiner

METHODS OF DETERMINING WATER DROPLET SIZE DISTRIBUTIONS OF CLOUDS

FIELD

The present invention relates to methods of determining water droplet size distributions of clouds.

BACKGROUND

The detection of airborne water droplets and their classification into a droplet size distribution is an important function in the operation of aircraft. Different cloud formations can present different water droplet size distributions and associated cloud liquid water content (LWC), thereby posing various risks to aircraft, such as icing. The water droplet size distribution and LWC of a cloud can be determined or estimated in various ways. Several existing methods are based on diffractive droplet sizing techniques. However, such diffractive sizing techniques are limited to a maximum detectable droplet diameter due to the small angle scattering of large water droplets. For example, diffractive scattering by large droplets at angles within the divergence angle of the probing laser beam is unresolvable from the laser beam itself with current detection systems. As a result, information regarding the presence of a distribution of large droplets in excess of the maximum resolvable diameter is lost, potentially leading to errors in the determination of the water droplet size distribution and associated LWC of a cloud.

SUMMARY

In one aspect, methods of determining the water droplet size distribution of a cloud are described herein, the method accounting for the presence of droplets exceeding the maximum detectable droplet diameter. Moreover, methods described herein contemplate estimating the LWC of the cloud using the determined water droplet size distribution.

In some embodiments, a method of determining a size distribution of water droplets in a cloud comprises sampling a depth of the cloud with a beam of electromagnetic radiation, measuring a scattering signal $[p_{total}(\theta)]$ of the electromagnetic radiation returned from the cloud over a range of field of view angles to provide a measured scattering curve, removing a portion of the measured scattering curve, replacing the removed portion with an extrapolation of the remaining measured scattering curve to provide an estimated scattering curve, and determining a first estimate droplet size distribution $[n^{(1)}(D)]$ from the estimated scattering curve. In some embodiments, the first estimate droplet size distribution is determined using a forward scattering model.

In some embodiments, the method further comprises providing a calculated scattering curve from $n^{(1)}(D)$ using a direct backscatter model and a forward scattering model and comparing the calculated scattering curve with the measured scattering curve to determine whether the calculated scattering curve follows the measured scattering curve within a set tolerance. In some embodiments wherein the calculated scattering curve does not follow the measured scattering curve within the set tolerance, a first estimate of a droplet median volume diameter $(D_{MVD}^{(1)})$ and shape parameter $(\mu^{(1)})$ are derived from $n^{(1)}(D)$. The value of $D_{MVD}^{(1)}$ is altered in response to the calculated scattering curve not following the measured scattering curve within the set tolerance to provide a second estimate of the droplet median volume diameter $D_{MVD}^{(2)}$. A second estimate water droplet size distribution $[n^{(2)}(D)]$ is provided using $D_{MVD}^{(2)}$ and $\mu^{(1)}$.

A second calculated scattering curve is provided from $n^{(2)}(D)$ using the direct backscatter model and the forward scatter model, and the second calculated scattering curve is compared with the measured scattering curve to determine whether the second scattering curve follows the measured scattering curve within the set tolerance. In some embodiments, the second calculated scattering curve follows the measured scattering curve within the set tolerance, and $n^{(2)}(D)$ accounts for the distribution of water droplets having a diameter beyond the maximum detectable droplet diameter. In such embodiments, the method can further comprise determining the effective droplet diameter $(D_{eff})$ using $n^{(2)}(D)$ and determining the liquid water content of the cloud using $D_{eff}$.

Alternatively, the second calculated scattering curve does not follow the measured scattering curve within the set tolerance, and the method comprises additional steps. In some embodiments, for example, the method further comprises altering the value of $D_{MVD}^{(2)}$ in response to the second calculated scattering curve not following the measured scattering curve within the set tolerance to provide a third estimate of the droplet median volume diameter $(D_{MVD}^{(3)})$. A third estimate water droplet size distribution $[n^{(3)}(D)]$ is provided using $D_{MVD}^{(3)}$ and $\mu^{(1)}$.

A third calculated scattering curve is provided from $n^{(3)}(D)$ using the direct backscatter model and the forward scattering model, and the third calculated scattering curve is compared with the measured scattering curve to determine whether the third scattering curve follows the measured scattering curve within the set tolerance. In some embodiments, the third calculated scattering curve follows the measured scattering curve within the set tolerance, and $n^{(3)}(D)$ accounts for the distribution of water droplets having a diameter beyond the maximum detectable droplet diameter. In such embodiments, the method can further comprise determining the effective droplet diameter $(D_{eff})$ using $n^{(3)}(D)$ and determining the liquid water content of the cloud using $D_{eff}$.

Alternatively, the third calculated scattering curve does not follow the measured scattering curve within the set tolerance, and the method comprises additional steps. For example, in some embodiments, the method is an iterative method comprising iterative steps that are repeated until a calculated scattering curve follows the measured scattering curve within the set tolerance. Therefore, in some embodiments, the method further comprises altering the value of $D_{MVD}^{(n)}$ in response to an $n^{th}$ calculated scattering curve not following the measured scattering curve within the set tolerance to provide an n+1 estimate of the droplet median volume diameter $[D_{MVD}^{(n+1)}]$, wherein n is an integer greater than 3. A (n+1) estimate droplet size distribution $[n^{(n+1)}(D)]$ is provided using $D_{MVD}^{(n+1)}$ and $\mu^{(1)}$.

A (n+1) calculated scattering curve is provided from $n^{(n+1)}(D)$ using the direct backscatter model and the forward scattering model, the (n+1) calculated scattering curve following the measured scattering curve within the set tolerance, and $n^{(n+1)}(D)$ accounts for the distribution of water droplets having a diameter beyond the maximum detectable droplet diameter. In some embodiments, the method further comprises determining $D_{eff}$ using $n^{(n+1)}(D)$ and determining the LWC of the cloud using $\mu^{(1)}$.

These and other embodiments are described in greater detail in the detailed description which follows.

DETAILED DESCRIPTION

Figure 1:
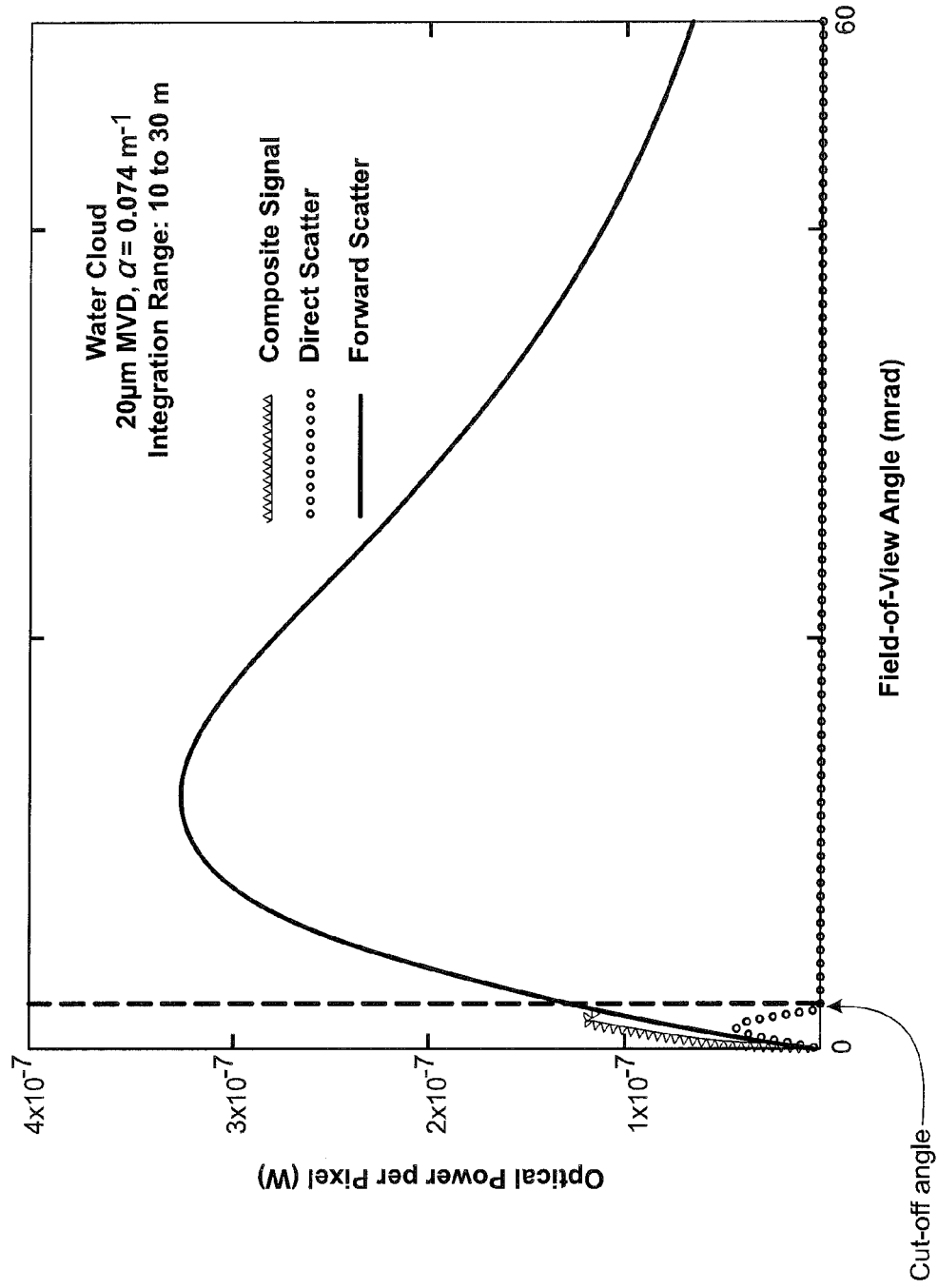
FIG. 1 illustrates one example of a measured scattering curve according to some embodiments described herein.

Embodiments described herein can be understood more readily by reference to the following detailed description and drawings. Elements, apparatus, and methods described herein, however, are not limited to the specific embodiments presented in the detailed description and drawings. It should be recognized that these embodiments are merely illustrative of the principles of the present invention. Numerous modifications and adaptations will be readily apparent to those of skill in the art without departing from the spirit and scope of the invention.

In one aspect, methods of determining the water droplet size distribution of a cloud are described herein, the method accounting for the presence of droplets exceeding a maximum detectable droplet diameter. Moreover, methods described herein contemplate estimating the LWC of the cloud using the determined water droplet size distribution.

Turning now to specific steps of a method described herein, a method described herein comprises sampling a depth of a cloud with electromagnetic radiation. A cloud can be sampled with electromagnetic radiation to any depth not inconsistent with the objectives of the present invention. In some embodiments, the cloud is sampled to a depth no greater than the distance over which the cloud is homogeneous or substantially homogeneous. In some embodiments, the cloud is sampled to a depth of up to about 30 meters (m). In some embodiments, the cloud is sampled to a depth of up to about 20 m. In some embodiments, the cloud is sampled to a depth between about 10 m and about 30 m. The cloud, in some embodiments, is sampled to a depth greater than 30 m.

The beam of electromagnetic radiation can comprise any beam not inconsistent with the objectives of the present invention. In some embodiments, the beam of electromagnetic radiation comprises a beam emitted from a laser. In some embodiments, the beam is polarized. In some embodiments, the beam is linearly polarized or circularly polarized. In some embodiments, the beam comprises a pulsed laser beam or a continuous wave laser beam. In some embodiments, the continuous wave laser beam is chopped. Moreover, in some embodiments, the beam of electromagnetic radiation is emitted from a light emitting diode.

The beam of electromagnetic radiation can comprise any wavelength distribution not inconsistent with the objectives of the present invention. In some embodiments, for example, the beam is a monochromatic or substantially monochromatic beam. In some embodiments, the beam of electromagnetic radiation has a wavelength in the infrared (IR) region of the electromagnetic spectrum including, but not limited to, the near infrared (NIR) region of the spectrum. In some embodiments, the beam of electromagnetic radiation has a wavelength in the visible region of the spectrum or the ultraviolet (UV) region of the spectrum. The beam of electromagnetic radiation, in some embodiments, has a wavelength not absorbed or substantially absorbed by water. In some embodiments, the beam of electromagnetic radiation has one or more wavelengths falling in an optical window not absorbed by water. In some embodiments, for example, the beam of electromagnetic radiation has a wavelength of about 905 nm.

Moreover, the beam of electromagnetic radiation can have any power not inconsistent with the objectives of the present invention. In some embodiments, the beam of electromagnetic radiation has a power or mW to tens of Mw.

As described herein, a scattering signal [$p_{total}(\theta)$] of the electromagnetic radiation returned from the cloud is measured over a range of field of view (FOV) angles to provide a measured scattering curve. The scattering signal can be measured with any suitable detector or detection system operable to resolve angular dependencies of the scattering signal. In some embodiments, the detector comprises a solid state photodetector, such as a photodiode array or concentric photodiode. The photodiode, in some embodiments, comprises one or more of silicon (Si), germanium (Ge), indium gallium arsenide ($InGa_xAs_{1-x}$), lead (II) sulfide (PbS), and combinations thereof. In some embodiments, the detector comprises at least one photosensitive element and one or more circuits for processing the output of the at least one photosensitive element. The one or more circuits, in some embodiments, comprise filtering circuits and/or amplification circuits.

Moreover, the range of FOV angles over which the scattering signal is measured can comprise any range of FOV angles not inconsistent with the objectives of the present invention. In some embodiments, the range of FOV angles is about 0 mrad to about 60 mrad or about 0 mrad to about 90 mrad.

In some embodiments, sampling a depth of the cloud and measuring the scattering signal is conducted with a single apparatus. In some embodiments, an apparatus used for sampling a depth of the cloud and measuring the scattering signal is coupled to an aircraft. In some embodiments, sampling the depth of the cloud and measuring the scattering signal is conducted while the aircraft is in-flight. A non-limiting apparatus for sampling a depth of the cloud and measuring the scattering signal is disclosed in United States Patent Application Publication 2011/0019188, the entirety of which is hereby incorporated by reference. Alternatively, sampling the depth of the cloud and measuring the scattering signal can be conducted with more than one apparatus. Where appropriate, one or more apparatus used to sample the depth of the cloud and measure the scattering signal can also be used to obtain other information about the cloud, in addition to determining the droplet size distribution and/or LWC of the cloud.

Further, methods described herein comprise removing a portion of the measured scattering curve and replacing the removed portion with an extrapolation of the remaining measured scattering curve to provide an estimated scattering curve. Removing and replacing a portion of the measured scattering curve can be conducted in any manner not inconsistent with the objectives of the present invention. In some embodiments, for instance, the measured scattering curve is removed at FOV angles below a cut-off angle. In some embodiments, the cut-off angle is the divergence angle of the beam of electromagnetic radiation. In some embodiments, the cut-off angle is greater than the divergence angle of the beam of electromagnetic radiation. The cut-off angle can be varied according to various considerations including, but not limited to, the amount of direct backscatter and/or diffractive scatter to remove from the measured scattering curve.

In some embodiments, the removed portion of the measured scattering curve comprises signal corresponding to direct backscatter of the electromagnetic radiation [$p_{direct}(\theta)$], and the remaining measured scattering curve comprises signal corresponding to forward scatter of the electromagnetic radiation [$p_{scat}(\theta)$]. In some embodiments, the removed portion of the measured scattering curve comprises signal corresponding to direct backscatter of the electromagnetic radiation below a cut-off angle. In some embodiments, the cut-off angle is chosen to ensure removal of all or substantially all of $p_{direct}(\theta)$.

Moreover, extrapolating the remaining measured scattering curve can be carried out in any manner not inconsistent with the objectives of the preset invention. In some embodiments, the extrapolation comprises a linear extrapolation. In some embodiments, the extrapolation comprises a parabolic extrapolation or a monotonic extrapolation. In some embodiments, the extrapolation comprises a spline function. The extrapolation of the remaining measured scattering curve satisfies the conditions of meeting the remaining scattering curve at the cut-off angle and vanishing at $\theta=0$.

Figure 2:
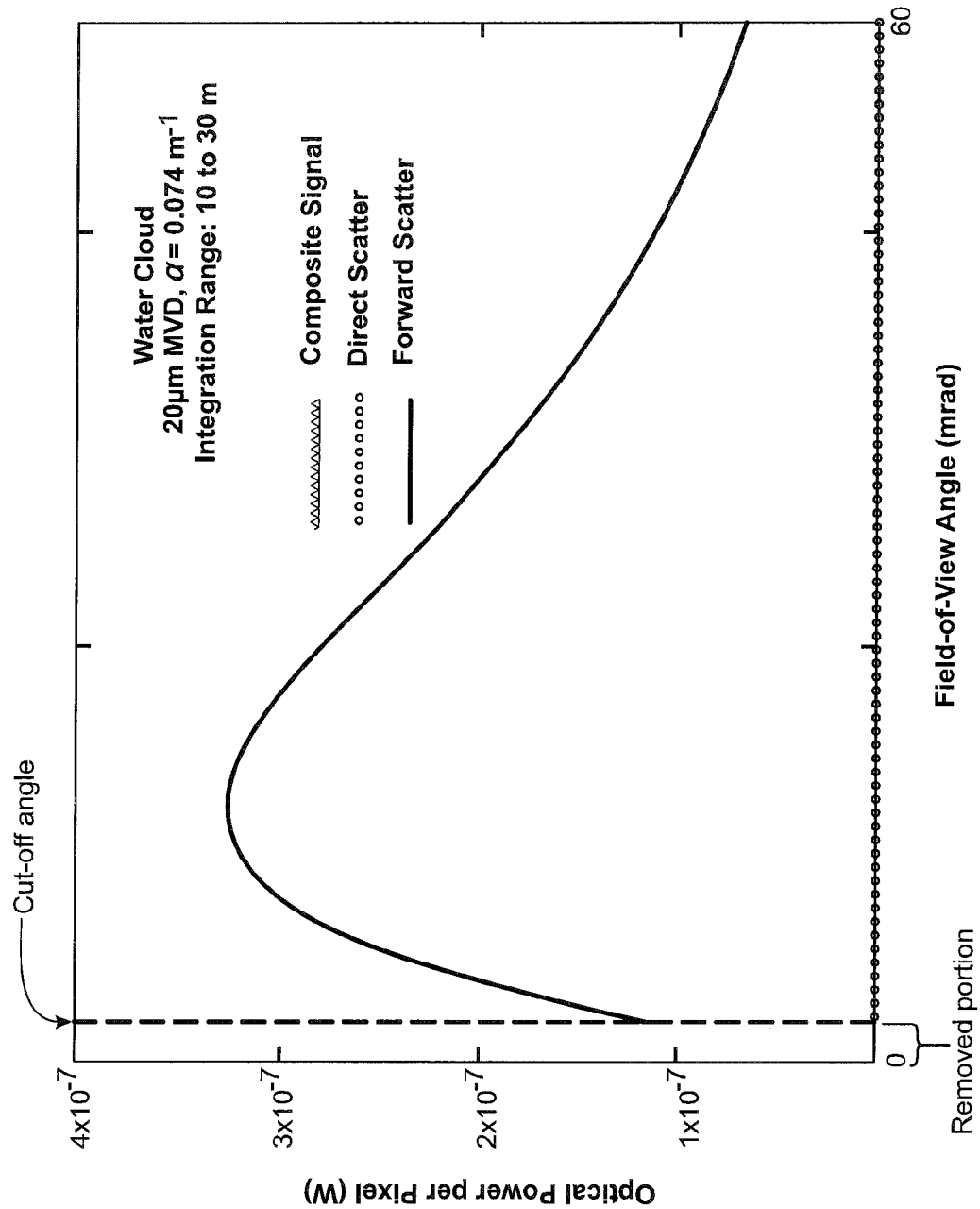
FIG. 2 illustrates the measured scattering curve of FIG. 1, wherein a portion of the measured scattering curve has been removed according to some embodiments described herein.
Figure 3:
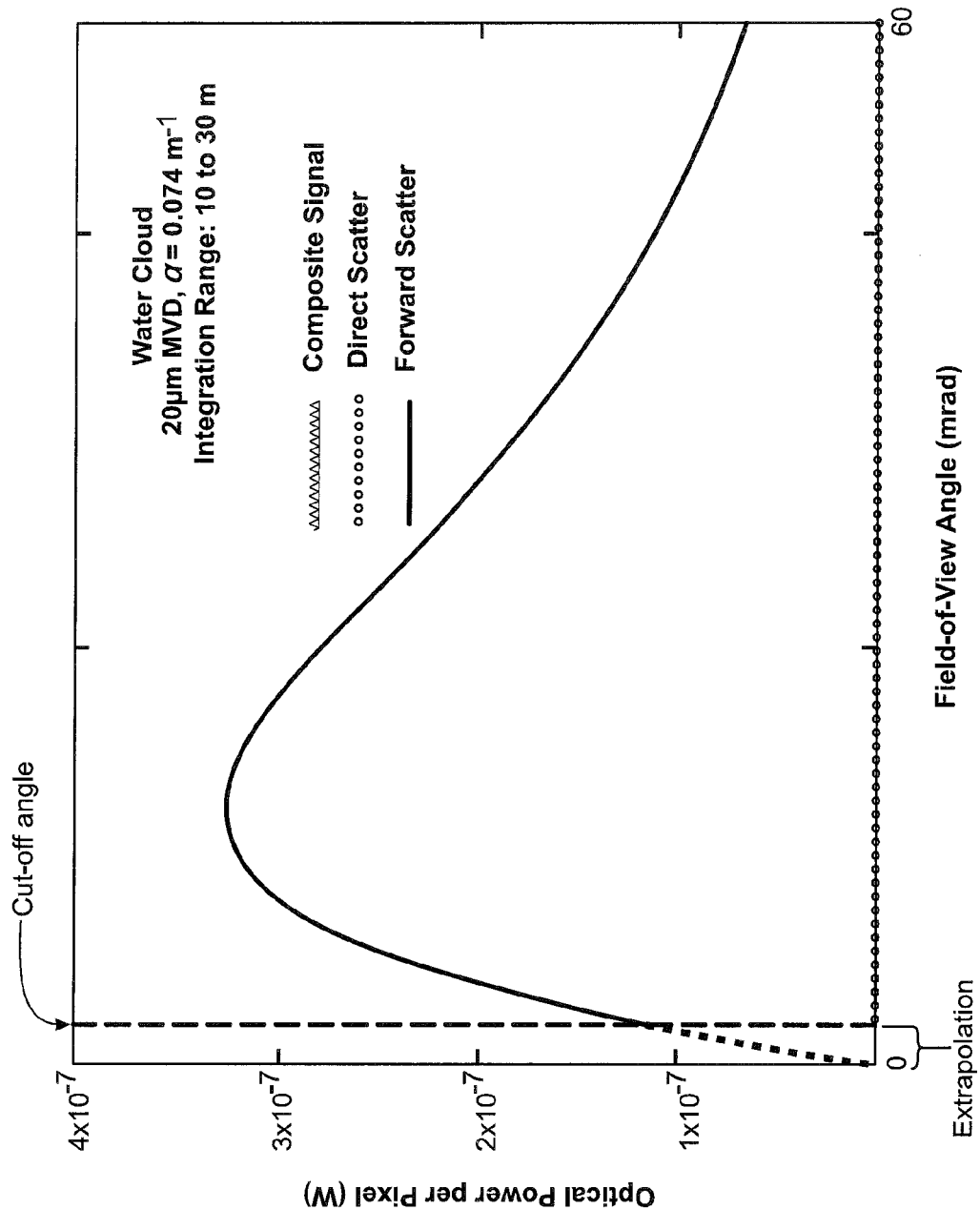
FIG. 3 illustrates the measured scattering curve of FIG. 2, wherein the removed portion has been replaced with an extrapolation of the remaining measured scattering curve according to some embodiments described herein.
Figure 4:
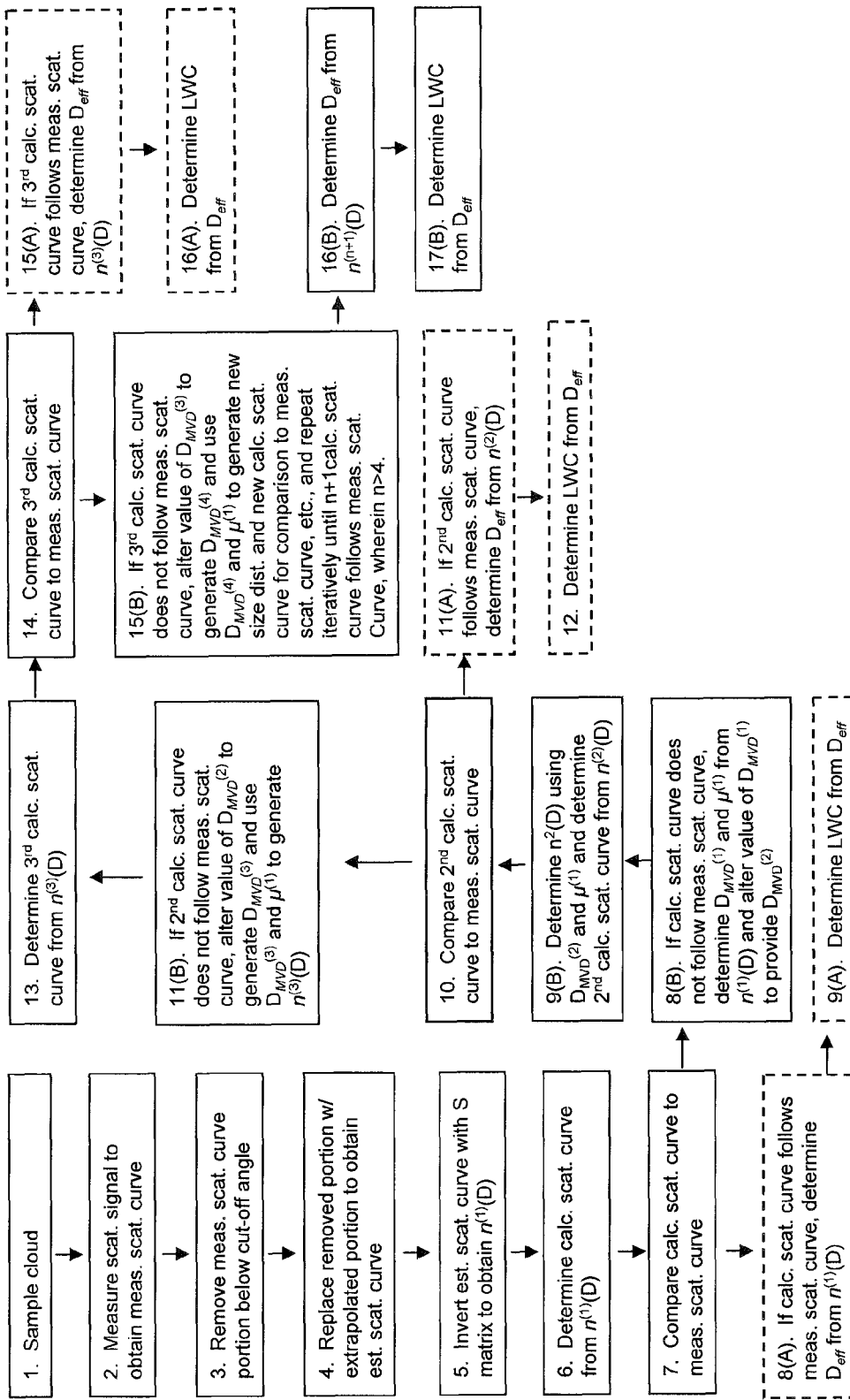
FIG. 4 is a flow chart illustrating one embodiment of a method described herein.

FIGS. 1-3 demonstrate a non-limiting example of a measured scattering curve and subsequent operation on the measured scattering curve to remove a portion of the curve and replacing the removed portion with an extrapolation to provide an estimated scattering curve. As illustrated in FIG. 1, the measured scattering curve at FOV angles below the cut-off angle is a composite (triangular line) of the direct backscatter of the laser beam from the sampled droplets (dotted curve) and the forward diffractive scatter of the droplets (solid curve). The measured scattering curve at FOV angles less than the cut-off angle is removed and replaced with a linear extrapolation of the remaining measured scattering curve as illustrated in FIGS. 2 and 3 respectively. The linear extrapolation satisfies the bounding conditions of coinciding or substantially coinciding with the remaining measured scattering curve at the cut-off angle and vanishing or substantially vanishing at $\theta=0$ to complete the estimated scattering curve.

A first estimate droplet size distribution $[n^{(1)}(D)]$ is determined from the estimated scattering curve. Determining $n^{(1)}(D)$ from the estimated scattering curve can be carried out in any manner not inconsistent with the objectives of the present invention. In some embodiments, $n^{(1)}(D)$ is determined from the estimated scattering curve using a forward scattering model. In some embodiments, the estimated scattering curve provides a first estimate of the forward scatter of the electromagnetic radiation $[p^{(1)}_{scat}(\theta)]$, and $n^{(1)}(D)$ is determined according to the function:

$$p^{(1)}_{scat}(\theta) = Sn^{(1)}(D), \quad (1)$$

wherein S is a matrix incorporating the forward scattering model. Any suitable forward scattering model may be used. Forward scattering models suitable for use in some embodiments described herein are described, for example, in Hogan, R. J., "Fast approximate calculation of multiply scattered lidar returns," *Applied Optics*, 2006, 45 (23), pp. 5984-5992, and Eloranta, E. W., "Practical model for the calculation of multiply scattered lidar returns," *Applied Optics*, 1998, 37 (12), pp. 2464-2472, the entireties of which are hereby incorporated by reference (hereinafter "Hogan" and "Eloranta," respectively).

A scattering curve is calculated from $n^{(1)}(D)$ using a direct backscatter model and the forward scattering model. Providing a calculated scattering curve from $n^{(1)}(D)$ using a direct backscatter model and the forward scattering model can be carried out in any manner not inconsistent with the objectives of the present invention. In some embodiments, the calculated scattering curve is determined according to the function:

$$p^{(1)}_{total}(\theta) = (S+C)n^{(1)}(D), \quad (2)$$

wherein C is a matrix incorporating a direct backscatter model and S is a matrix incorporating the forward scatter model. Any suitable direct backscatter model and forward scatter model may be used. Direct backscatter models suitable for use in some embodiments described herein are described, for example, in Hogan and Eloranta. Further, the matrix C, in some embodiments, includes elements associated with one or more of the divergence of the beam of electromagnetic radiation, the focal length of the detector optics, and the geometry of the sampled cloud range.

The scattering curve calculated from $n^{(1)}(D)$ is compared with the measured scattering curve to determine whether the calculated scattering curve follows the measured scattering curve within a set tolerance. Comparing the curves can be administered in any desired manner. For example, in some embodiments, the comparison is made using the entire calculated scattering curve and the entire measured scattering curve. In some embodiments, only a portion of the calculated scattering curve is compared with a portion of the measured scattering curve. In some embodiments, for example, comparison of the curves is administered at small angles, such as angles below the cut-off angle.

Moreover, the set tolerance can comprise any desired tolerance not inconsistent with the objectives of the present invention. In some embodiments, the set tolerance comprises agreement between the calculated scattering curve and the measured scattering curve based on a standard reduced $\chi$-squared test, as discussed, for example, in John Mandel, *The Statistical Analysis of Experimental Data*, Dover Publications (1964), the entirety of which is hereby incorporated by reference. The reduced $\chi$-squared can be expressed as follows:

$$\tilde{\chi}^2 = \frac{1}{(N-2)} \sum_{k=1}^{N} \frac{(p^{(n)}_{total}(\theta_k) - p_{total}(\theta_k))^2}{p_{total}(\theta_k)}, \quad (3)$$

wherein the index k denotes the range of FOV, and (N−2) is the number of degrees of freedom. The number of degrees of freedom is the number of measured points of $p_{total}(\theta_k)$ minus the two fit parameters of $D_{MVD}$ and m for the droplet distribution. The computed $\tilde{\chi}^2$ for (N−2) degrees of freedom is compared to previously tabulated values of $Prob_{N-2}(\chi^2 \geq \tilde{\chi}^2)$ using a table of reduced $\chi$-squared values to determine the probability of obtaining a value of $\chi^2$ at least as large as $\tilde{\chi}^2$ (i.e., the probability of agreement). The acceptable probability level can vary based on the signal-to-noise ratio. In some embodiments, the acceptable probability of agreement is at least about 70 percent. In some embodiments, the acceptable probability of agreement is at least about 80 percent or at least about 90 percent. In some embodiments, the acceptable probability of agreement is at least about 95 percent.

In some embodiments, the scattering curve calculated from $n^{(1)}(D)$ follows the measured scattering curve within the set tolerance. In such embodiments, the method can further comprise determining $D_{eff}$ using $n^{(1)}(D)$ and determining the LWC of the cloud using $D_{eff}$ as described further hereinbelow.

In some embodiments, the scattering curve calculated from $n^{(1)}(D)$ does not follow the measured scattering curve within the set tolerance. In some embodiments wherein the calculated scattering curve does not follow the measured scattering curve within the set tolerance, a first estimate of a droplet median volume diameter ($D_{MVD}^{(1)}$) and shape parameter ($\mu^{(1)}$) are derived from $n^{(1)}(D)$. Determining $D_{MVD}^{(1)}$ and $\mu^{(1)}$ from $n^{(1)}(D)$ can be carried out in any manner not inconsistent with the objectives of the present invention. For example, in some embodiments, $D_{MVD}^{(1)}$ can be determined according to the equation:

$$\frac{\int_0^{D_{MVD}^{(1)}} D^3 n^{(1)}(D) \, dD}{\int_0^{\infty} D^3 n^{(1)}(D) \, dD} = 1/2. \quad (4)$$

Moreover, in some embodiments, $\mu^{(1)}$ is determined according to the equation:

$$\mu^{(1)} = \frac{\ln\left(\frac{n^{(1)}(D_1)}{n^{(1)}(D_2)}\right)}{\ln\left(\frac{D_1}{D_2}\right)}, \quad (5)$$

wherein $D_1$ is a first chosen droplet diameter less than $D_{MVD}^{(1)}$ and $D_2$ is a second chosen droplet diameter less than $D_{MVD}^{(1)}$. In some embodiments, $D_1$ and $D_2$ are small enough for any exponential portion of $n^{(1)}(D)$ to be considered the same for $D_1$ and $D_2$. Some possible exponential components of droplet size distributions are described, for example, in Shah, A. D., "Droplet Size Distribution and Ice shapes," American Institute of Aeronautics and Astronautics (AIAA) International Conference of Aircraft Inflight Icing, May 1996, pp. 1-20, the entirety of which is hereby incorporated by reference.

The value of $D_{MVD}^{(1)}$ is altered in response to the calculated scattering curve not following the measured scattering curve within the set tolerance to provide a second estimate of the droplet median volume diameter ($D_{MVD}^{(2)}$). In some embodiments, the value of $D_{MVD}^{(1)}$ is increased to provide $D_{MVD}^{(2)}$. In some embodiments, the value of $D_{MVD}^{(1)}$ is decreased to provide $D_{MVD}^{(2)}$. For example, in some embodiments, the value of $D_{MVD}^{(1)}$ can be decreased or increased based on whether the calculated scattering curve fails to follow the measured scattering curve within the set tolerance by being too high at small scattering angles or too low at small scattering angles.

A second estimate water droplet size distribution [$n^{(2)}(D)$] is provided using $D_{MVD}^{(2)}$ and $\mu^{(1)}$. In some embodiments, $n^{(2)}(D)$ is provided according to the equation:

$$n^{(2)}(D) = n_0 \left(\frac{D}{D_{MVD}^{(2)}}\right)^{\mu^{(1)}} \exp\left(\frac{-(3.67 + \mu^{(1)})D}{D_{MVD}^{(2)}}\right) \quad (6)$$

wherein $n_o$ is the droplet number concentration per united of droplet diameter in $m^{-3} \, \mu m^{-1}$. In some embodiments, $n_o$ is measured. In some embodiments, $n_o$ is determined according to the equation:

$$n_0 = 4.35 \cdot 10^{[6-4\mu^{(1)}]} (D_{MVD}^{(2)})^{\mu^{(1)}} e^{7.05\mu^{(1)}}. \quad (7)$$

A second calculated scattering curve is provided from $n^{(2)}(D)$ using the direct backscatter model and the forward scattering model and compared with the measured scattering curve to determine whether the second calculated scattering curve follows the measured scattering curve within the set tolerance. Providing the second calculated scattering curve from $n^{(2)}(D)$ using the direct backscatter model and the forward scattering model can be carried out in any desired manner. In some embodiments, for example, the second calculated scattering curve is determined according to the function:

$$p^{(2)}_{total}(\theta) = (S+C)n^{(2)}(D), \quad (8)$$

wherein S and C are as described herein. Further, comparing the second calculated scattering curve to the measured scattering curve can be carried out in any desired manner. For example, in some embodiments, the curves can be compared using an $\chi$-squared test as described herein.

In some embodiments, the second calculated scattering curve follows the measured scattering curve within the set tolerance, and $n^{(2)}(D)$ accounts for the distribution of water droplets having a diameter beyond the maximum detectable droplet diameter. In such embodiments, the method can further comprise determining the effective droplet diameter ($D_{eff}$) using $n^{(2)}(D)$ and determining the liquid water content of the cloud using $D_{eff}$.

Alternatively, the second calculated scattering curve provided from $n^{(2)}(D)$ does not follow the measured scattering curve within the set tolerance and the method comprises additional steps. The method, in some embodiments, further comprises altering the value of $D_{MVD}^{(2)}$ in response to the second calculated scattering curve not following the measured scattering curve within the set tolerance to provide a third estimate of the droplet median volume diameter ($D_{MVD}^{(3)}$). In some embodiments, the value of $D_{MVD}^{(2)}$ is increased to provide $D_{MVD}^{(3)}$. In some embodiments, the value of $D_{MVD}^{(2)}$ is decreased to provide $D_{MVD}^{(3)}$. For example, in some embodiments, the value of $D_{MVD}^{(2)}$ can be decreased or increased based on whether the second calculated scattering curve fails to follow the measured scattering curve within the set tolerance by being too high at small scattering angles or too low at small scattering angles.

$D_{MVD}^{(3)}$ is used in conjunction with $\mu^{(1)}$ to provide a third estimate droplet size distribution [$n^{(3)}(D)$]. In some embodiments, $n^{(3)}(D)$ is provided according to the equation:

$$n^{(3)}(D) = n_0 \left(\frac{D}{D_{MVD}^{(3)}}\right)^{\mu^{(1)}} \exp\left(\frac{-(3.67 + \mu^{(1)})D}{D_{MVD}^{(3)}}\right) \quad (9)$$

wherein $n_o$ is the droplet number concentration per united of droplet diameter in $m^{-3} \, \mu m^{-1}$. In some embodiments, $n_o$ is measured. In some embodiments, $n_o$ is determined according to the equation:

$$n_0 = 4.35 \cdot 10^{[6-4\mu^{(1)}]} (D_{MVD}^{(2)})^{\mu^{(1)}} e^{7.05\mu^{(1)}} \quad (10)$$

A third calculated scattering curve is determined from $n^{(3)}(D)$ using the direct backscatter model and the forward scattering model and compared with the measured scattering curve to determine whether the third scattering curve follows the measured scattering curve within the set tolerance. Providing the third calculated scattering curve from $n^{(3)}(D)$ using the direct backscatter model and the forward scattering model can be carried out in any manner not inconsistent with the objectives of the present invention. In some embodiments, for example, the third calculated scattering curve is determined according to the function:

$$p^{(3)}_{total}(\theta) = (S+C)n^{(3)}(D) \quad (11)$$

wherein S and C are as described herein. Further, comparing the third calculated scattering curve to the measured scattering curve can be carried out in any desired manner. For example, in some embodiments, the curves can be compared using an $\chi$-squared test as described herein.

In some embodiments, the third calculated scattering curve follows the measured scattering curve within the set tolerance, and $n^{(3)}(D)$ accounts for the distribution of water droplets having a diameter beyond the maximum detectable droplet diameter. In such embodiments, the method can further comprise determining the effective droplet diameter ($D_{eff}$) using $n^{(3)}(D)$ and determining the liquid water content of the cloud using $D_{eff}$ as described herein below.

Alternatively, the third calculated scattering curve provided from $n^{(3)}(D)$ does not follow the measured scattering curve within the set tolerance, and the method comprises additional steps, including iterative steps. For example, in some embodiments, methods described herein further comprise altering the value of $D_{MVD}^{(n)}$ in response to an $n^{th}$ calculated scattering curve not following the measured scattering curve within the set tolerance to provide an n+1 estimate of the droplet median volume diameter $[D_{MVD}^{(n+1)}]$, wherein n is an integer greater than 3. In some embodiments, the value of $D_{MVD}^{(n)}$ is increased or decreased to provide $D_{MVD}^{(n+1)}$. The $n^{th}$ calculated scattering curve, in some embodiments, is determined from $n^{(n)}(D)$ using the direct backscatter model and forward scattering model as described herein.

$D_{MVD}^{(n+1)}$ is used in conjunction with $\mu^{(1)}$ to provide an (n+1) estimate droplet size distribution $[n^{(n+1)}(D)]$. In some embodiments, $n^{(n+1)}(D)$ is determined according to the equation:

$$n^{(n+1)}(D) = n_0 \left(\frac{D}{D_{MVD}^{(n+1)}}\right)^{\mu^{(1)}} \exp\left(\frac{-(3.67 + \mu^{(1)})D}{D_{MVD}^{(n+1)}}\right) \quad (12)$$

wherein $n_o$ is the droplet number concentration per united of droplet diameter in $m^{-3} \mu m^{-1}$. In some embodiments, $n_o$ is measured. In some embodiments, $n_o$ is determined according to the equation:

$$n_o = 4.35 \cdot 10^{[6-4\mu(1)]} (D_{MVD}^{(n+1)})^{\mu(1)} e^{7.05\mu(1)}. \quad (13)$$

A (n+1) calculated scattering curve is determined from $n^{(n+1)}(D)$ using the direct backscatter model and the forward scattering model and compared with the measured scattering curve to determine whether the (n+1) calculated scattering curve follows the measured scattering curve within the set tolerance. Providing the (n+1) scattering curve from $n^{(n+1)}(D)$ using the direct backscatter model and the forward scattering model, in some embodiments, is determined according to the function $$p^{(n+1)}_{total}(\theta) = (S+C)n^{(n+1)}(D), \quad (14)$$

wherein S and C are as described herein. Further, as described herein, comparing the (n+1) calculated scattering curve to the measured scattering curve can be carried out in any desired manner. For example, in some embodiments, the curves can be compared using an $\chi$-squared test described herein.

In some embodiments, the (n+1) calculated scattering curve follows the measured scattering curve within the set tolerance, and $n^{(n+1)}(D)$ accounts for the distribution of water droplets having a diameter beyond the maximum detectable droplet diameter.

In some embodiments wherein the scattering curve calculated from $n^{(n+1)}(D)$ follows the measured scattering curve within the set tolerance, the method can further comprise determining $D_{eff}$ using $n^{(n+1)}(D)$ and determining LWC using $D_{eff}$.

In some embodiments of methods described herein, $D_{eff}$ is determined according to the equation:

$$D_{eff} = \frac{\int_0^\infty D^3 n(D)\, dD}{\int_0^\infty D^2 n(D)\, dD}, \quad (15)$$

wherein n(D) is the desired estimate droplet size distribution [e.g. $n^{(1)}(D)$, $n^{(2)}(D)$, $n^{(3)}(D)$ or $n^{(n+1)}(D)$].

Moreover, methods described herein can further comprise determining the LWC of the cloud using $D_{eff}$. In some embodiments, the LWC is determined according to the equation:

$$LWC = 3\rho\alpha D_{eff}, \quad (16)$$

wherein $\rho$ is the density of water and $\alpha$ is the optical extinction coefficient. In some embodiments, for example, the optical extinction coefficient is measured. In some embodiments, the optical extinction coefficient is calculated or inferred.

FIG. 5 illustrates a flow chart of a method according to one embodiment described herein.

It is contemplated that methods described herein can be at least in part executed and/or implemented on computer or processor-based systems. In some embodiments, the computer or processor-based systems are part of an aircraft operating system.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A method of determining a size distribution of water droplets in a cloud comprising:
    sampling a depth of a could with a beam of electromagnetic radiation, the beam of electromagnetic radiation comprising a beam emitted from a laser;
    measuring a scattering signal of the electromagnetic radiation returned from the cloud over a range of a field of view angles $p_{total}(\theta)$ to provide a measured scattering curve;
    removing a portion of the measured scattering curve;
    replacing the removed portion with an extrapolation of the remaining measured scattering curve to provide an estimated scattering curve;
    determining a first estimate droplet size distribution $n^{(1)}(D)$ from the estimated scattering curve using a forward scattering model;
    providing a calculated scattering curve from $n^{(1)}(D)$ using a direct backscatter model and the forward scattering model;
    comparing the calculated scattering curve with the measured scattering curve to determine whether the calculated scattering curve follows the measured scattering curve within a set tolerance;
    determining a first estimate of a droplet median volume diameter $(D_{MVD}^{(1)})$ from $n^{(1)}(D)$ and determining a first estimate of a shape parameter $(\mu^{(1)})$ from $n^{(1)}(D)$; and
    altering the value of $D_{MVD}^{(1)}$ in response to the calculated scattering curve not following the measured scattering curve within the set tolerance to provide a second estimate of the droplet median volume diameter $D_{MVD}^{(2)}$, and using $D_{MVD}^{(2)}$ and $\mu^{(1)}$ to provide a second estimate droplet size distribution $n^{(2)}(D)$.

2. The method of claim 1 further comprising providing a second calculated scattering curve from $n^{(2)}(D)$ using the direct backscatter model and the forward scattering model and comparing the second calculated scattering curve with the measured scattering curve to determine whether the second scattering curve follows the measured scattering curve within the set of tolerance.

3. The method of claim 2 further comprising altering the value of $D_{MVD}^{(2)}$ in response to the second calculated scattering curve not following the measured scattering curve within the set tolerance to provide a third estimate of the droplet median volume diameter ($D_{MVD}^{(3)}$).

4. The method of claim 3 further comprising providing a third estimate droplet size distribution $n^{(3)}(D)$ using $D_{MVD}^{(3)}$ and $\mu^{(1)}$.

5. The method of claim 4 further comprising providing a third calculated scattering curve from $n^{(3)}(D)$ using the direct backscatter model and the forward scattering model, and comparing the third calculated scattering curve with the measured scattering curve to determine whether the third scattering curve follows the measured scattering curve within the set tolerance.

6. The method of claim 5, wherein the portion of the measured scattering curve is removed at field of view angles below a cut-off angle.

7. The method of claim 6, wherein the cut-off angle is the divergence angle of the beam of electromagnetic radiation.

8. The method of claim 6, wherein the extrapolation of the remaining measured scattering curve satisfies the conditions of meeting the remaining scattering curve at the cut-off angle and vanishing at $\theta=0$.

9. The method of claim 6, wherein the removed portion of the measured scattering curve comprises signal corresponding to direct backscatter of the electromagnetic radiation $p_{direct}(\theta)$ and the remaining measured scattering curve comprises signal corresponding to forward scatter of the electromagnetic radiation $p_{scat}(\theta)$.

10. The method of claim 9, wherein the estimated scattering curve provides a first estimate of the forward scatter of the electromagnetic radiation $p^{(1)}_{scat}(\theta)$.

11. The method of claim 10, wherein $n^{(1)}(D)$ is determined according to the function:

$$p^{(1)}\text{scat}(\theta)=Sn^{(1)}(D)$$

wherein S is a matrix incorporating the forward scattering model.

12. The method of claim 11, wherein the calculated scattering curve is determined according to the function:

$$p^{(1)}_{total}(\theta)=(S+C)n^{(1)}(D)$$

wherein C is a matrix incorporating a direct backscatter model.

13. The method of claim 11, wherein $D_{MVD}^{(1)}$ is determined according to the equation:

$$\frac{\int_0^{D_{MVD}^{(1)}} D^3 n^{(1)}(D)\,dD}{\int_0^\infty D^3 n^{(1)}(D)\,dD} = 1/2.$$

14. The method of claim 11, wherein $\mu^{(1)}$ is determined according to the equation:

$$\mu^{(1)} = \frac{\ln\left(\frac{n^{(1)}(D_1)}{n^{(1)}(D_2)}\right)}{\ln\left(\frac{D_1}{D_2}\right)}$$

wherein $D_1$ is a first droplet diameter less than $D_{MVD}^{(1)}$ and $D_2$ is a second droplet diameter less than $D_{MVD}^{(1)}$.

15. The method of claim 14, wherein the third calculated scattering curve follows the measured scattering curve within the set tolerance, and $n^{(3)}(D)$ accounts for the distribution of water droplets having a diameter beyond the maximum detectable droplet diameter.

16. The method of claim 15, wherein the third calculated scattering curve is determined according to the function:

$$p^{(3)}_{total}(\theta)=(S+C)n^{(3)}(D).$$

17. The method of claim 16 further comprising determining the liquid water content of the cloud using $D_{eff}$.

18. The method of claim 17 further comprising determining the effective droplet diameter ($D_{eff}$) using $n^{(3)}(D)$.

19. The method of claim 5 further comprising altering the value of $D_{MVD}^{(n)}$ in response to an $n^{th}$ calculated scattering curve not following the measured scattering curve within the set tolerance to provide an n+1 estimate of the droplet median volume diameter $D_{MVD}^{(n+1)}$), wherein n is an integer greater than 3.

20. The method of claim 19 further comprising providing a (n+1) estimate droplet size distribution $n^{(n+1)}(D)$ using $D_{MVD}^{(n+1)}$ and $\mu^{(1)}$.

21. The method of claim 20 further comprising providing a (n+1) calculated scattering curve from $n^{(n+1)}(D)$ using the direct backscatter model and the forward scattering model, the (n+1) calculated scattering curve following the measured scattering curve within the set tolerance.

22. The method of claim 21 further comprising determining the effective droplet diameter ($D_{eff}$) using $n^{(n+1)}(D)$.

23. The method of claim 22 further comprising determining the liquid water content of the cloud using $D_{eff}$.

24. The method of claim 21, wherein the portion of the measured scattering curve is removed at field of view angles below a cut-off angle.

25. The method of claim 24, wherein the cut-off angle is the divergence angle of the beam of electromagnetic radiation.

26. The method of claim 25, wherein the removed portion of the measured scattering curve comprises signal corresponding to direct backscatter of the electromagnetic radiation $p_{direct}(\theta)$ and the remaining measured scattering curve comprises signal corresponding to forward scatter of the electromagnetic radiation $p_{scat}(\theta)$.

27. The method of claim 26, wherein the estimated scattering curve provides a first estimate of the forward scatter of the electromagnetic radiation $p^{(1)}_{scat}(\theta)$.

28. The method of claim 27, wherein $n^{(1)}(D)$ is determined according to the function:

$$p^{(1)}_{scat}(\theta)=Sn^{(1)}(D)$$

wherein S is a matrix incorporating the forward scattering model.

29. The method of claim 28, wherein the calculated scattering curve is determined according to the function:

$$p^{(1)}\text{total}(\theta)(S+C)n^{(1)}(D)$$

wherein C is a matrix incorporating a direct backscatter model.

30. The method of claim 28, wherein $D_{MVD}^{(1)}$ is determined according to the equation:

$$\frac{\int_0^{D_{MVD}^{(1)}} D^3 n^{(1)}(D)\,dD}{\int_0^\infty D^3 n^{(1)}(D)\,dD} = 1/2.$$

31. The method of claim 30, wherein $\mu(1)$ is determined according to the equation:

$$\mu^{(1)} = \frac{\ln\left(\frac{n^{(1)}(D_1)}{n^{(1)}(D_2)}\right)}{\ln\left(\frac{D_1}{D_2}\right)}$$

wherein $D_1$ is a first droplet diameter less than $D_{MVD}^{(1)}$ and $D_2$ is a second droplet diameter less than $D_{MVD}^{(1)}$.

* * * * *